(12) United States Patent
Lee et al.

(10) Patent No.: US 8,481,293 B2
(45) Date of Patent: Jul. 9, 2013

(54) MUTANT MICROORGANISMS HAVING A HIGH ABILITY TO PRODUCE PUTRESCINE AND METHOD FOR PRODUCING PUTRESCINE USING THE SAME

(75) Inventors: Sang Yup Lee, Daejeon (KR); Zhi Gang Qian, Daejeon (KR); Xiaoxia Xia, Daejeon (KR); Yong Jae Jeon, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 185 days.

(21) Appl. No.: 12/579,052

(22) Filed: Oct. 14, 2009

(65) Prior Publication Data

US 2010/0203599 A1 Aug. 12, 2010

Related U.S. Application Data

(63) Continuation of application No. PCT/KR2009/001103, filed on Mar. 5, 2009.

(30) Foreign Application Priority Data

Apr. 10, 2008 (KR) ........................ 10-2008-0033125

(51) Int. Cl.
*C12P 13/00* (2006.01)
*C12N 9/00* (2006.01)
*C12N 1/00* (2006.01)
*C12N 1/20* (2006.01)
*C12N 15/00* (2006.01)
*C07H 21/04* (2006.01)

(52) U.S. Cl.
USPC ........ 435/128; 435/183; 435/243; 435/252.3; 435/320.1; 536/23.2

(58) Field of Classification Search
None
See application file for complete search history.

(56) References Cited

FOREIGN PATENT DOCUMENTS

WO 2006-005604 A1 1/2006
WO WO-2006/005603 A1 1/2006

OTHER PUBLICATIONS

Bowman et al. J Biol Chem. Apr. 10, 1973;248(7):2480-6.*
Fukuchi et al. J Biol Chem. Aug. 11, 1995;270(32):18831-5.*
Lee et al. Biotechnol Lett. Nov. 2006;28(22):1849-56. Epub Aug. 25, 2006.*
Kurihara et al. J Biol Chem. Feb. 11, 2005;280(6):4602-8. Epub Dec. 8, 2004.*
Samsonova et al. BMC Microbiol. Jan. 31, 2003;3(1):2.*
Kashiwagi et al. J Bacteriol. Jul. 1988;170(7):3131-5.*
Tkachenko et al., "The Role of the Natural Polyamine Putrescine in Defense Against Oxidative Stress in *Escherichia coli*", Arch. Microbiol., 176:155-157 (2001).
Kashiwagi et al., "Adjustment of Polyamine Contents in *Escherichia coli*", J. Bacteriol., 170(7):3131-3135 (1998).
Sakata et al., "Properties of a Polyamine Transporter Regulated by Antizyme", Biochem. J., 347:297-303 (2000).
Bowman et al., "Spermidine Biosynthesis: Purification and Properties of Propylamine Transferase from *Escherichia coli*", J. Biol. Chem., 248:2480-2486 (1973).
Haywood et al., "The Occurence, Subcellular Localization and Partial Purification of Diamine Acetyltransferase in the Yeast *Candida boidinii* Grown on Spermidine or Putrescine as Sole Nitrogen Source", Eur. J. Biochem., 148:277-283 (1985).
Samsonova et al., "Molecular Cloning and Characterization of *Escherichia coli* K12 ygjG Gene", BMC Microbiol., 3:2 (2003).
Samsonova et al., "Identification of *Escherichia coli* K12 YdcW Protein as a Y-Aminobutyraldehyde Dehydrogenase", FEBS Lett., 579:4107-4112 (2005).
Kurihara et al., "A Novel Putrescine Utilization Pathway Involves γ-Glutamylated Intermediates of *Escherichia coli* K-12", J. Biol. Chem., 280:4602-4608 (2005).
J.M. Kim et al., "Development of a Markerless Gene Knock-Out System for Mannheimia Succiniciproducens Using a Temperature-Sensitive Plasmid", FEMS Microbiol. Lett., 278:78-85 (2008).
Palmeros et al., "A Family of Removable Cassettes Designed to Obtain Antibiotic-Resistance-Free Genomic Modifications of *Escherichia coli* and Other Bacteria", Gene, 247(1):255-264 (2000).
Lee et al., "High Cell Density Cultivation of *Escherichia coli* W Using Sucrose as a Carbon Source", Biotechnol. Lett., 15:971-974 (1993).
Qian et al., "Proteome-Based Identification of Fusion Partner for High-Level Extracellular Production of Recombinant Proteins in *Escherichia coli*", Biotechnol. and Bioeng., 101(3):587-601 (2008).
Tabor et al., "Spermidine synthase of *Escherichia coli*: Localization of the speE gene," Proc. Natl. Acad. Sci. USA, vol. 83, No. 16, pp. 6040-6044 (1986).
Official Action for Russian Application No. 2009144119/13(062753) issued by Russian Patent Office on Nov. 24, 2010.
Kashiwagi et al., "Coexistence of the Genes for Putrescine Transport Protein and Ornithine Decarboxylase at 16 min on *Escherichia coli* Chromosome," J. Biol. Chem., vol. 266, No. 31, pp. 20922-20927 (1991).
Tholl et al., "Retarded growth of an *Escherichia coli* mutant deficient in spermidine synthase can be unspecifically repaired by addition of various polyamines," World Jrl. of Microbiology and Biotechnology, 14, pp. 857-863, (1998).

* cited by examiner

*Primary Examiner* — Christian Fronda
(74) *Attorney, Agent, or Firm* — Rabin & Berdo, P.C.

(57) ABSTRACT

Provided are mutant microorganisms having the ability to produce a high concentration of putrescine wherein gene(s) involved in the putrescine degradation or utilization pathway is inactivated or deleted and a preparation method thereof. A method for producing putrescine in high yield by culturing the mutant microorganisms is also provided. The mutant microorganisms are useful for producing a high concentration of putrescine which can be widely used in various industrial applications.

24 Claims, 5 Drawing Sheets

MUTANT MICROORGANISMS HAVING A HIGH ABILITY TO PRODUCE PUTRESCINE AND METHOD FOR PRODUCING PUTRESCINE USING THE SAME

CROSS-REFERENCES TO RELATED APPLICATIONS

This application is a continuation of PCT/KR2009/001103 filed on Mar. 5, 2009 which claims priority to Korean Application No. 10-2008-0033125 filed on Apr. 10, 2008. The entire contents of the aforementioned patent applications are incorporated herein by this reference.

BACKGROUND

1. Technical Field

The present invention relates to a mutant microorganism having the ability to produce a high concentration of putrescine and a method for producing putrescine using the same. More particularly, the present invention relates to a mutant microorganism having the ability to produce a high concentration of putrescine wherein gene(s) involved in the putrescine degradation or utilization pathway is inactivated or deleted, and a method for producing putrescine in high yield by culturing the microorganism.

2. Related Art

Putrescine (also known as 1,4-butanediamine), an important raw material for the production of polyamide-4,6, including nylon-4,6, is mainly produced on industrial scale by the hydrogenation of succinonitrile which is produced into acrylonitrile by addition of hydrogen cyanide. Known processes for the chemical synthesis of this compound require non-renewable petrochemical products as raw materials, and relatively severe reaction conditions of temperature and pressure in a multi-step and multi-reactor design, as well as the use of expensive catalyst systems. Furthermore, because these raw materials are highly toxic and flammable, the known chemical synthetic processes are environmentally disadvantageous. Accordingly, as an alternative to the chemical production process, a process of producing putrescine from a renewable biomass-derived carbon source is required.

Putrescine is a kind of polyamine which is found in a broad spectrum of organisms ranging from bacteria to animals and plants. For example, putrescine is known to play an important role not only in cell proliferation and normal cell growth, but also in a defensive mechanism against oxidative stress (Tkachenko et al., *Arch. Microbiol.*, 176:155-157, 2001). Meanwhile, the intracellular levels of polyamines are strictly controlled by their biosynthesis, degradation, uptake, and secretion (Igarashi and Kashiwagi et al., *J. Bacteriol.*, 170(7): 3131-3135, 1988). The concentration of putrescine in *E. coli* is known to be as extremely high as about 2.8 g/l. Also, microorganisms have potentially good resistance to high concentrations of polyamines. For example, Mimitsuka et al. have reported that *Corynebacterium glutamicum* can grow even in the presence of more than 30 g/L of cadaverine. Accordingly, studies on the production of high-concentration polyamines (putrescine) using microorganisms have been continued.

European Patent Publication No. 0726240 A1 discloses a method of producing putrescine through fermentation using inexpensive industrial waste products or materials having protein as a major component. However, because the disclosed materials are very complex, there is a problem in that many purification steps have to be carried out in order to obtain putrescine and cadaverine. In addition, European Patent Publication No. 1784496 A1 discloses a process of biochemically synthesizing putrescine by microbial growth in a minimal salt medium containing glucose as a carbon source. According to this patent document, in order to improve the conversion of ornithine to putrescine, the activity of ornithine decarboxylase is increased by overexpression of an ornithine decarboxylase-encoding speC or speF. However, when the putrescine content is increased as a result of increasing ornithine decarboxylase, there are problems in that putrescine biosynthesis is inhibited and the degradation of putrescine is induced (Igarashi and Kashiwagi et al., *Biochem. J.*, 347:297-303, 2000).

Studies on the degradation and utilization of putrescine in microorganisms are as follows. Bowman et al. have reported that spermidine synthase which is the product of the speE gene promotes the biosynthesis of spermidine from putrescine in *E. coli* (Bowman et al., *J. Biol. Chem.*, 248: 2480-2486, 1973). Spermidine synthase (EC:2.5.1.16) is present in most cell systems for the synthesis of spermidine.

Haywood et al. have reported that the yeast *Candida boidinii* induces the acetylation of putrescine to N-acetylputrescine in the presence of N-acetyltransferase. Spermidine acetyltransferase which is an *E. coli* speG gene product has high homology with the N-acetyltransferase of the yeast, and thus, must possess putrescine acetyltransferase (Haywood and Large, *Eur. J. Biochem.*, 148:277-283, 1985).

Furthermore, Samsonova et al. have reported another putrescine degradation pathway in which a coupling action of *E. coli* YgjG putrescine transaminase and YdcW dehydrogenase without γ-glutamylation results in conversion of putrescine into γ-aminobutyric acid (Samsonova et al., *BMC Microbiol.*, 3:2, 2003; Samsonova et al., *FEBS Lett.*, 579: 4107-4112, 2005).

Moreover, Kurihara et al. have called the putrescine degradation pathway as "Puu catabolic pathway" based on the findings that the putrescine degradation pathway is closely associated with γ-glutamylated metabolites of *E. coli*. Through such γ-glutamylation, γ-aminobutyraldehyde which is an aldehyde intermediate can be stabilized. The first reaction of this pathway is promoted by converting putrescine to γ-glutamyl-L-putrescine in the presence of γ-glutamylputrescine synthetase which is the product of the puuA gene. Also, it has been found that the catabolic pathway is a major factor for culturing *E. coli* in a medium containing putrescine as a sole nitrogen source. In addition, it has been found that a putrescine importer which is the product of the puuP gene is associated with the catabolic pathway and main putrescine importers (Kurihara et al., *J. Biol. Chem.*, 280:4602-4608, 2005).

Accordingly, the present inventors have prepared mutant microorganisms wherein at least one gene selected from a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway of putrescine-producing microorganisms, is inactivated or deleted, and have found that, when the mutant microorganisms are cultured, they can produce a high concentration of putrescine, thereby completing the present invention.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

It is an object of the present invention to provide a mutant microorganism having the ability to produce a high concentration of putrescine wherein at least one gene involved in the putrescine degradation or utilization pathway is inactivated or deleted, and a method of preparing the microorganism.

Another object of the present invention is to provide a method for producing putrescine in high yield by culturing the microorganism.

To achieve the above objects, the present invention provides a mutant microorganism having the ability to produce putrescine wherein at least one gene selected from the group consisting of a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway, is inactivated or deleted, and a preparation method thereof.

The present invention also provides a mutant microorganism having the ability to produce putrescine wherein at least one gene selected from the group consisting of a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway, is inactivated or deleted and wherein a promoter of at least one gene selected from the group consisting of an argECBH gene encoding an operon for arginine biosynthesis, an argD gene encoding acetylornithine aminotransferase, and a speF-potE gene encoding inducible ornithine decarboxylase and putrescine/ornithine antiporter is replaced with a strong promoter, and a preparation method thereof.

The present invention also provides a mutant microorganism having the ability to produce putrescine wherein at least one gene selected from the group consisting of a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway, is inactivated or deleted, wherein a promoter of at least one gene selected from the group consisting of an argECBH gene encoding an operon for arginine biosynthesis, an argD gene encoding acetylornithine aminotransferase, and a speF-potE gene encoding inducible ornithine decarboxylase and putrescine/ornithine antiporter is replaced with a strong promoter, and wherein a speC gene encoding ornithine decarboxylase is introduced or amplified, and a preparation method thereof.

The present invention also provides a method for producing putrescine, the method including: culturing the above-described mutant microorganism to produce putrescine and recovering putrescine from the culture broth.

Other features and aspects of the present invention will be apparent from the following detailed description and the appended claims.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE EMBODIMENTS

As used herein, the term "inactivation (inactivated)" is meant to comprehend the mutation, substitution (replacement) or deletion of one or more bases of a target gene or the introduction of one or more bases into the gene, so as to reduce the activity of an enzyme which is expressed by the gene, thereby partially or wholly blocking the biosynthetic pathway in which the enzyme is involved.

As used herein, the term "deletion (deleted)" is meant to comprehend the mutation, substitution (replacement) or deletion of the whole or a part of a target gene or the introduction of one or more bases into the gene, so that the gene is not expressed or does not exhibit enzymatic activity, and further, so that, even though it is expressed, the gene-associated biosynthetic pathway is blocked.

As used herein, the term "amplification (amplified)" is meant to comprehend the mutation, substitution (replacement) or deletion of one or more bases of a target gene, the introduction of one or more bases into the gene or the introduction of another microbial gene encoding the same enzyme, so as to increase the activity of the corresponding enzyme.

Figure 1:
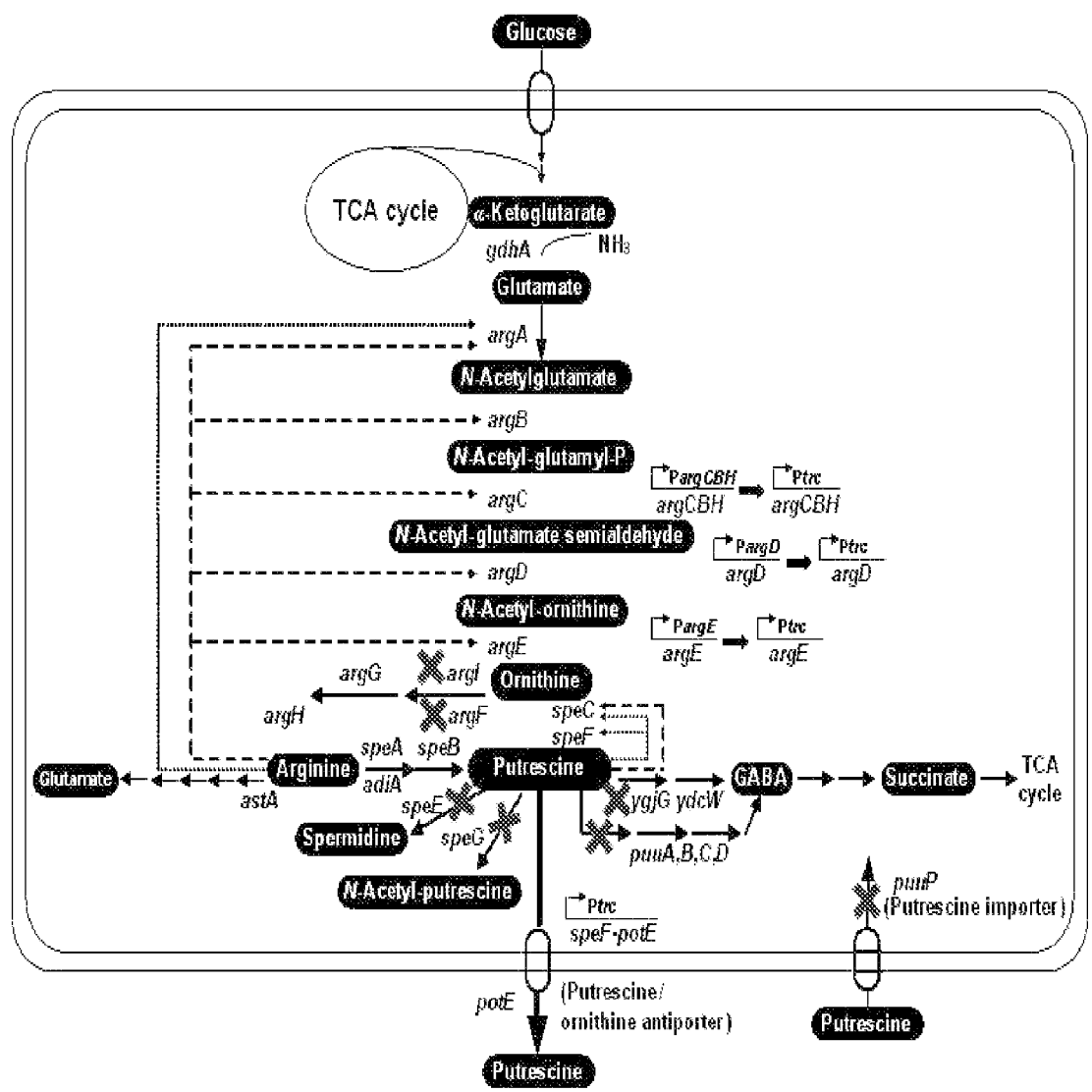
FIG. 1 is a schematic diagram showing a pathway for the synthesis of putrescine from glucose.

FIG. 1 is a schematic diagram showing a pathway for the synthesis of putrescine from glucose. As shown in FIG. 1, the present inventors have found that, when gene(s) (speE, speG, argI, and puuP) involved in the putrescine degradation or utilization pathway of a putrescine-producing microorganism is inactivated or deleted, putrescine can be produced in high yield. Reduced activities of the genes (speE, speG, argI, and puuP) involved in the putrescine degradation or utilization pathway could be confirmed by reduced transcriptional and translational efficiency as compared to those of the respective wild-type genes.

In Examples of the present invention, the present inventors prepared mutant microorganisms wherein at least one gene selected from the group consisting of a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway, was deleted, and found that the microorganisms had an improved ability to produce putrescine.

Accordingly, in one aspect, the present invention provides a mutant microorganism having the ability to produce putrescine wherein at least one gene selected from the group consisting of the speE gene encoding spermidine synthase, the speG gene encoding spermidine N-acetyltransferase, the argI gene encoding ornithine carbamoyltransferase chain I-monomer and the puuP gene encoding putrescine importer, which are involved in the putrescine degradation or utilization pathway, is inactivated or deleted, and a preparation method thereof.

In the inventive mutant microorganism, at least one gene selected from the group consisting of a puuA gene encoding γ-glutamylputrescine synthase, a ygjG gene encoding putrescine transaminase and an argF gene encoding ornithine carbamoyltransferase chain F-monomer may be further inactivated or deleted.

The argF gene encoding ornithine carbamoyltransferase chain F-monomer, argI gene encoding ornithine carbamoyltransferase chain I-monomer, and the puuA gene encoding γ-glutamylputrescine synthase is a neighboring gene of the puuP gene encoding putrescine importer. The ygjG gene encoding putrescine transaminase is a gene which is involved in putrescine degradation.

In the inventive mutant microorganism, a lacI gene encoding a lac operon repressor may also be further deleted in order to increase the expression of genes encoding enzymes which are involved in putrescine biosynthesis. Examples of the genes encoding the enzymes which are involved in putrescine biosynthesis include gdhA, argA, argB, argC, argD, argE, etc.

In the inventive mutant microorganism, a speC gene encoding ornithine decarboxylase may also be further introduced or amplified. The speC gene encoding ornithine decarboxylase is introduced in the form of an expression vector containing a strong promoter. The strong promoter may be selected from the group consisting of a trc promoter, a tac promoter, a T7 promoter, a lac promoter and a trp promoter.

As the inventive microorganism, any microorganism may be used without particular limitation, as long as it produces putrescine from glucose. Examples of the microorganism include *Bacillus* sp., *Corynebacterium* sp., *Escherichia* sp., *Pichia* sp., *Pseudomonas* sp., *Saccharomyces* sp., etc.

The present inventors have also found that, in a mutant microorganism wherein the gene(s) involved in the putrescine degradation or utilization pathway is deleted, when the promoter of at least one gene selected from the group consisting of an argECBH gene encoding an operon for arginine biosynthesis, an argD gene encoding acetylornithine aminotransferase, and a speF-potE gene encoding inducible ornithine decarboxylase and putrescine/ornithine antiporter is replaced with a strong promoter, the resulting microorganism can produce a higher concentration of putrescine.

In Examples of the present invention, based on a mutant microorganism wherein the gene(s) (speE, speG, argI, puuP) involved in the putrescine degradation or utilization pathway and the lacI gene encoding the lac operon repressor were deleted, the present inventors prepared the following microorganisms: a microorganism (XQ33) in which the promoter of the argECBH gene encoding an operon for arginine biosynthesis was replaced with a strong promoter (trc); a microorganism (XQ37) in which the promoters of the argECBH gene and the speF-potE gene encoding inducible ornithine decarboxylase and putrescine/ornithine antiporter were replaced with the strong promoter trc; a microorganism (XQ39) in which the promoters of the argECBH gene, the speF-potE gene and the argD gene encoding acetylornithine aminotransferase were replaced with the strong promoter trc; and a microorganism (XQ43) in which the promoters of the argECBH gene, the speF-potE gene, the argD gene and the speC gene encoding ornithine decarboxylase were replaced with the strong promoter (trc), and found that these microorganisms produced a significantly increased concentration of putrescine.

Accordingly, in another aspect, the present invention provides a mutant microorganism having the ability to produce putrescne wherein at least one gene selected from the group consisting of the speE gene encoding spermidine synthase, the speG gene encoding spermidine N-acetyltransferase, the argI gene encoding ornithine carbamoyltransferase chain I-monomer and the puuP gene encoding putrescine importer, which are involved in a putrescine degradation or utilization pathway, is inactivated or deleted, and wherein the promoter of at least one gene selected from the group consisting of the argECBH gene encoding an operon for arginine biosynthesis, the argD gene encoding acetylornithine aminotransferase and the speF-potE gene encoding inducible ornithine decarboxylase and putrescine/ornithine antiporter is replaced with a strong promoter, and a preparation method thereof.

In the present invention, the argECBH gene encoding the operon for arginine biosynthesis is a divergent operon flanked by two convergent promoters (argEp and argCBHp) and containing an operator. The two promoters are suppressed by arginine (Charlier and Glansdorff, 2004). Thus, when the native promoter of the argECBH operon is replaced with the strong promoter, the metabolic flux to ornithine can be increased. The argE gene is a gene encoding N-acetylornithinase, the argC gene is a gene encoding N-acetylglutamylphosphate reductase, the argB gene is a gene encoding N-acetylglutamate kinase, and the argH gene is a gene encoding argininosuccinase.

The speF-potE gene encoding inducible ornithine decarboxylase and putrescine/ornithine antiporter, which is induced at low pH, encodes inducible ornithine decarboxylase and putrescine/ornithine antiporter. Thus, when the native promoter of the speF-potE operon is replaced with the strong promoter, the speF-potE operon can be constitutively expressed, thereby improving the ability to produce putrescine.

The promoter of the argD gene encoding acetylornithine aminotransferase is suppressed by arginine (Charlier and Glansdorff, 2004). Thus, when the native promoter of the argD operon is replaced with the strong promoter, the metabolic flux to ornithine can be increased.

As described above, in the inventive mutant microorganism, at least one gene selected from the group consisting of the puuA gene encoding γ-glutamylputrescine synthase, the ygjG gene encoding putrescine transaminase and the argF gene encoding ornithine carbamoyltransferase chain F-monomer may be further inactivated or deleted.

In the mutant microorganism having the ability to produce putrescine, the lacI gene encoding the lac operon repressor may be further deleted to increase the expression of genes encoding enzymes involved in putrescine biosynthesis.

In the present invention, the speC gene encoding ornithine decarboxylase may be introduced in the form of an expression vector containing a strong promoter.

In the present invention, the strong promoter which is used as a substitute for the gene promoter as well as in the introduction of the speC gene encoding ornithine decarboxylase may be selected from the group consisting of a trc promoter, a tac promoter, a T7 promoter, a lac promoter and a trp promoter.

The most preferred example of the inventive mutant microorganism may be a mutant microorganism having the ability to produce putrescine wherein at least one gene selected from the group consisting of the speE gene encoding spermidine synthase, the speG gene encoding spermidine N-acetyltransferase, the argI gene encoding ornithine carbamoyltransferase chain I-monomer and the puuP gene encoding putrescine importer, which are involved in the putrescine degradation or utilization pathway, is inactivated or deleted, wherein the promoter of at least one gene selected from the group consisting of the argECBH gene encoding an operon for arginine biosynthesis, the argD gene encoding acetylornithine aminotransferase and the speF-potE gene encoding inducible ornithine decarboxylase and putrescine/ornithine antiporter is replaced with a strong promoter, and wherein the speC gene encoding ornithine decarboxylase is introduced or amplified.

In still another aspect, the present invention provides a method for producing putrescine, the method comprising: culturing the above-described mutant microorganism to produce putrescine, and recovering putrescine from the culture broth.

In the present invention, the culture of the mutant microorganism and the recovery of putrescine from the culture broth can be carried out using a culture method (batch culture or fed-batch culture) known in conventional fermentation processes, and putrescine separation and purification methods known in the art.

In the present invention, the biosynthetic production of putrescine can be carried out in vivo or in vitro.

Hereinafter, the present invention will be described in further detail with reference to examples. It is to be understood, however, that these examples are for illustrative purposes only and are not to be construed to limit the scope of the present invention.

Particularly, although only specific kinds of vectors for removing target genes and the putrescine-producing microorganisms of *Escherichia* sp. serving as host cells were illustrated in the following examples, it will also be obvious to a person skilled in the art to use other types of vectors and putrescine-producing microorganisms.

EXAMPLE 1

Preparation of Mutant Microorganisms Wherein Gene(s) Involved in the Putrescine Degradation or Utilization Pathway is Deleted In the present invention, the deletion of gene(s) (puuA, puuP, ygjG, speE, speG, argF, argI) on the chromosomes was performed by double-crossover homologous recombination (Datsenko, K. A., & Wanner, B. L. *Proc. Natl. Acad. Sci.*, 97:6640-6645, 2000). A lox71-chloramphenicol marker (CmR)-lox66 cassette was prepared by PCR using primers containing 50 nucleotides homologous to the upstream and downstream regions of the target gene. pECmulox (Kim, J. M., Lee, K. H. & Lee, S. Y., *FEMS Microbiol. Lett.*, 278: 78-85, 2008) containing the lox71-CmR-lox66 cassette was used as a template in PCR. The PCR products were transformed into electrocompetent *E. coli* cells containing λ, recombinase. Colonies were selected on Luria-Bertani (LB) agar media containing 34 μg/ml of chloramphenicol (Cm) (Sambrook, J., Fritsch E. F., & Maniatis, T., Molecular cloning: a laboratory manual, 3rd edition, Cold Spring Harbor Laboratory Press, 2000). Successful gene replacement with $Cm^R$ was confirmed by direct colony PCR. The antibiotic marker was eliminated by a helper plasmid pJW168 containing a temperature-sensitive replication origin and expressing the IPTG-inducible cre recombinase (Palmeros et al., *Gene*, 247(1):255-264, 2000).

1-1: Preparation of WL3110 Strain

PCR was performed using plasmid pECmulox as a template and primers of SEQ ID NOS: 1 and 2 below to obtain a PCR product in which the lad gene was deleted. The PCR product was then purified and electroporated into electrocompetent *E. coli* (W3110) containing λ, recombinase, to thereby produce a WL3110 strain (W3110 ΔlacI).

[SEQ ID NO: 1]
5'-GTGAAACCAGTAACGTTATACGATRTCGCAGAGTATGCCGGTGTCTC
TTAGATTGGCAGCATTACACGTCTTG-3'

[SEQ ID NO: 2]
5'-TCACTGCCCGCTTTCCAGTCGGGAAACCTGTCGTGCCAGCTGCATTA
ATGCACTTAACGGCTGACATGGG-3'

1-2: Preparation of XQ08 Strain

PCR was performed using plasmid pECmulox as a template and primers of SEQ ID NOS: 3 and 4 below to obtain a PCR product in which the speE gene was deleted. The PCR product was then purified and electroporated into the WL3110 strain prepared in Example 1-1 to thereby produce a XQ08 strain (W3110 ΔlacI ΔspeE).

[SEQ ID NO: 3]
5'-CGCCTGAATAATTTCGGTTGAGAGATGGCGTAAGGCGTCGTTATCTG
TCGGACACTATAGAACGCGGCCG-3'

[SEQ ID NO: 4]
5'-ATGTTGCGCCCTTTTTTTACGGGTGTTAACAAAGGAGGTATCAACCC
ATGCCGCATAGGCCACTAGTGGA-3'

1-3: Preparation of XQ17 Strain

PCR was performed using plasmid pECmulox as a template and primers of SEQ ID NOS: 5 and 6 below to obtain a PCR product in which the puuA gene was deleted. The PCR product was then purified and electroporated into the WL3110 strain prepared in Example 1-1 to thereby produce a XQ17 strain (W3110 ΔlacI ΔpuuA).

[SEQ ID NO: 5]
5'-GATGAAACAACCCCGCAAGGGGTATTACGCGTTTTTCAACATCCACT
CAAGACACTATAGAACGCGGCCG-3'

[SEQ ID NO: 6]
5'-CGAGCGGAAAACAAACCAAAGGCGAAGAATCATGGAAACCAATATCG
TTGCCGCATAGGCCACTAGTGGA-3'

1-4: Preparation of XQ22 Strain

PCR was performed using plasmid pECmulox as a template and primers of SEQ ID NOS: 6 and 7 below to obtain a PCR product in which the puuP gene was deleted. The PCR product was then purified and electroporated into the XQ17 strain (W3110 ΔlacI ΔpuuA) prepared in Example 1-3 to thereby produce a XQ22 strain (W3110 ΔlacI ΔpuuP ΔpuuA).

[SEQ ID NO: 6]
5'-CGAGCGGAAAACAAACCAAAGGCGAAGAATCATGGAAACCAATATCG
TTGCCGCATAGGCCACTAGTGGA-3'

[SEQ ID NO: 7]
5'-TCACCATCATACAACGGCACTTTGCGATAGCGGCGGATCAGATACCA
TAAGACACTATAGAACGCGGCCG-3'

1-5: Preparation of XQ23 Strain

PCR was performed using plasmid pECmulox as a template and primers of SEQ ID NOS: 8 and 9 below to obtain a PCR product in which the speE gene was deleted. The PCR product was then purified and electroporated into the WL3110 strain prepared in Example 1-1 to thereby produce a XQ23-1 strain (W3110 ΔlacI ΔspeE).

[SEQ ID NO: 8]
5'-CGCCTGAATAATTTCGGTTGAGAGATGGCGTAAGGCGTCGTTATCTG
TCGGACACTATAGAACGCGGCCG-3'

[SEQ ID NO: 9]
5'-ATGTTGCGCCCTTTTTTTACGGGTGTTAACAAAGGAGGTATCAACCC
ATGCCGCATAGGCCACTAGTGGA-3'

PCR was performed using plasmid pECmulox as a template and primers of SEQ ID NOS: 10 and 11 below to obtain a PCR product in which the speG gene was deleted. The PCR product was then purified and electroporated into the above-prepared XQ23-1 strain (W3110 ΔlacI ΔspeE) to thereby produce a XQ23-2 strain (W3110 ΔlacI ΔspeE ΔspeG).

[SEQ ID NO: 10]
5'-GAATGTAAGGACACGTTATGCCAAGCGCCCACAGTGTTAAGCTACGC
CCGGACACTATAGAACGCGGCCG-3'

[SEQ ID NO: 11]
5'-CTATTGTGCGGTCGGCTTCAGGAGAGTCTGACCCGGTGTTTTGTGCT
CTGCCGCATAGGCCACTAGTGGA-3'

PCR was performed using plasmid pECmulox as a template and primers of SEQ ID NOS: 12 and 13 below to obtain a PCR product in which the argI gene was deleted.

[SEQ ID NO: 12]
5'-TAATGTGATGCCGGGATGGTTTGTATTTCCCGGCATCTTTATAGCGA
TAGGACACTATAGAACGCGGCCG-3'

[SEQ ID NO: 13]
5'-CCATATAAATTGAATTTTAATTCATTGAGGCGTTAGCCACAGGAGGG
ATCCCGCATAGGCCACTAGTGGA-3'

Next, the PCR product was purified and PCR was then performed using the PCR product as a template and primers of SEQ ID NOS: 14 and 15 below. The resultant PCR product was purified and electroporated into the above-prepared XQ23-2 strain (W3110 ΔlacI ΔspeE ΔspeG) to thereby produce a XQ23 strain (W3110 ΔlacI ΔspeE ΔspeG ΔargI).

[SEQ ID NO: 14]
5'-ATAGCAATAGAACACTTTGGGTGGAAGAATAGACCTATCACTGC
ATAAAATAATGTGATGCCGGGATGGTT-3'

[SEQ ID NO: 15]
5'-CCACCTTTGTGACAAAGATTTATGCTTTAGACTTGCAAATGAAT
AATCATCCATATAAATTGAATTTTAA-3'

1-6: Preparation of XQ26 Strain

The PCR product with the deletion of the puuA gene prepared in Example 1-3 and the PCR product with the deletion of the puuP gene prepared in Example 1-4 were sequentially electroporated into the XQ23 strain (W3110 ΔlacI ΔspeE ΔspeG ΔargI) to thereby produce a XQ26 strain (W3110 ΔlacI ΔspeE ΔspeG ΔargI ΔpuuP ΔpuuA).

1-7: Preparation of XQ27 Strain

PCR was performed using plasmid pECmulox as a template and primers of SEQ ID NOS: 16 and 17 below to obtain a PCR product in which the ygjG gene was deleted.

[SEQ ID NO: 16]
5'-CTGCAATACTTAAATCGGTATCATGTGATACGCGAGCCTCCGGA
GCATATGACACTATAGAACGCGGCCG-3'

[SEQ ID NO: 17]
5'-CGTCGTATCGCCATCCGATTTGATATTACGCTTCTTCGACACTT
ACTCGCCCGCATAGGCCACTAGTGGA-3'

The PCR product was purified and electroporated into the XQ23-2 strain (W3110 ΔlacI ΔspeE ΔspeG) prepared in Example 1-5 to thereby obtain a XQ27-1 strain (W3110 ΔlacI ΔspeE ΔspeG ΔygjG). Then, the PCR product with the deletion of the puuA gene prepared in Example 1-3 and the PCR product with the deletion of the puuP gene prepared in Example 1-4 were sequentially electroporated into the XQ27-1 strain to thereby produce a XQ27 strain (W3110 ΔlacI ΔspeE ΔspeG ΔygjG ΔpuuP ΔpuuA).

1-8: Preparation of XQ29 Strain

The PCR product with the deletion of the ygjG gene prepared in Example 1-7 was electroporated into the XQ26 strain (W3110 ΔlacI ΔspeE ΔspeG ΔargI ΔpuuP ΔpuuA) prepared in Example 1-6 to thereby produce a XQ29 strain (W3110 ΔlacI ΔspeE ΔspeG ΔygjG ΔargI ΔpuuP ΔpuuA).

EXAMPLE 2

Replacement of Promoter

In order to improve the ability to produce putrescine, the promoter of the XQ26 strain prepared in Example 1 was replaced with a strong promoter (trc).

2-1: Preparation of XQ33 Strain

Replacement of the native promoter of the argECBH operon with the trc promoter was carried out as follows.

A DNA fragment of fused lox71-chloramphenicol antibiotic marker-lox66 was produced by first PCR using pECmulox as a template and primers of SEQ ID NOS: 18 and 19 below.

[SEQ ID NO: 18]
5'-TATCCGCTCACAATTCCACACATTATACGAGCCGGATGATTAAT
TGTCAACAGCTGACACTATAGAACGCGGCCG-3'

[SEQ ID NO: 19]
5'-TATCCGCTCACAATTCCACACATTATACGAGCCGGATGATTAAT
TGTCAACAGCTCCGCATAGGCCACTAGTGGA-3'

In order to introduce the trc promoter, second PCR was performed using the first PCR product as a template and primers of SEQ ID NOS: 20 and 21 below.

[SEQ ID NO: 20]
5'-CGCTGGCACCCACAATCAGCGTATTCAACATGGTCTGTTTCCTG
TGTGAAATTGTTATCCGCTCACAATTCCACA-3'

[SEQ ID NO: 21]
5'-TCTCGATAAATGGCGGTAATTTGTTTTTCATGGTCTGTTTCCTG
TGTGAAATTGTTATCCGCTCACAATTCCACA-3'

In order to introduce homologous regions into the final PCR product, third PCR was performed using the second PCR product as a template and primers of SEQ ID NOS: 22 and 23 below.

[SEQ ID NO: 22]
5'-ATGTTCATATGCGGATGGCGATTTACATAGGTCACTAGCTCTGC
GCCAGCGTAGCCGCTGGCACCCACAATCAGC-3'

[SEQ ID NO: 23]
5'-TCGAGTGCCTCTTCCGTGGCGCTTATTGAAGGTGTGGCAATCAG
AGCGCGGTAAATCTCGATAAATGGCGGTAAT-3'

The final PCR product was electroporated into the XQ26 strain (W3110 ΔlacI ΔspeE ΔspeG ΔargI ΔpuuP ΔpuuA) prepared in Example 1-6 to obtain transformed cell strains. The resultant cells were cultured on an agar medium containing chloramphenicol, and only cells in which double homologous recombination occurred were then selected, to thereby produce an XQ33 strain (W3110 ΔlacI ΔspeE ΔspeG ΔargI ΔpuuP ΔpuuA PargECBH::Ptrc). The presence of the trc promoter in the strain was confirmed by DNA sequence analysis.

2-2: Preparation of XQ37 Strain

Replacement of the native promoter of the speF-potE operon with the trc promoter was performed as follows.

First PCR was carried out using plasmid pECmulox as a template, the above-described primer of SEQ ID NO: 19 and a primer of SEQ ID NO: 24 below.

[SEQ ID NO: 24]
5'-ACTAAGGGCACTTCAGCGTACAGGTCTTCCTGACTCTCTGTAGA
CACTATAGAACGCGGCCG-3'

Second PCR was carried out using the first PCR product as a template and primers of SEQ ID NOS: 25 and 26 below.

[SEQ ID NO: 25]
5'-AGCTTCGACTTTCACTTCTTCAATGCCCGTTAGTCTACCGACTA
AGGGCACTTCAGCGTA-3'

[SEQ ID NO: 26]
5'-AATCACTAACCGCAATTTTTAATTTTGACATGGTCTGTTTCCT
GTGTGAAATTGTTATCCGCTCACAATTCCACA-3'

Third PCR was carried out using the second PCR product as a template and primers of SEQ ID NOS: 27 and 28 below.

[SEQ ID NO: 27]
5'-AAGGCGGACAACTCATATTATGAAGTTTGCTCATCGCAATAGCT
TCGACTTTCACTTCTT-3'

[SEQ ID NO: 28]
5'-CGACTTTCATTAATGTAGATACATTCTCGCTGCGTGGTAAAACA
GTCCGGGCAAGAATCACTAACCGCAATTTTTAA-3'

The final PCR product was electroporated into the XQ33 strain (W3110 ΔlacI ΔspeE ΔspeG ΔargI ΔpuuP ΔpuuA PargECBH::Ptrc) prepared in Example 2-1 to obtain transformed cell strains. The resultant cells were cultured on an agar medium containing chloramphenicol, and only cells in which double homologous recombination occurred were selected, to thereby produce an XQ37 strain (W3110 ΔlacI ΔspeE ΔspeG ΔargI ΔpuuP ΔpuuA PargECBH::Ptrc PspeF-potE::Ptrc). The presence of the trc promoter in the strain was confirmed by DNA sequence analysis.

2-3: Preparation of XQ39 Strain

Replacement of the native promoter of the argD operon with the trc promoter was performed as follows.

First PCR was performed using plasmid pECmulox as a template, the above-described primer of SEQ ID NO: 19 and a primer of SEQ ID NO: 29 below.

[SEQ ID NO: 29]
5'-CAACTGCTGGCTAATTTCCTGCATCGCTGATTTCTGATTGGACA
CTATAGAACGCGGCCG-3

Second PCR was performed using the first PCR product as a template and primers of SEQ ID NOS: 30 and 31 below.

[SEQ ID NO: 30]
5'-GCAGTTCCATCCAGAAAGTATTCTTAGCGAACAAGGACATCAA
CTGCTGGCTAATTTCCT-3'

[SEQ ID NO: 31]
5'-CGCGTGTAATTGCTGTTTGTTCAATTGCCATGGTCTGTTTCCT
GTGTGAAATTGTTATCCGCTCACAATTCCACA-3'

Third PCR was performed using the first PCR product as a template and primers of SEQ ID NOS: 32 and 33 below.

[SEQ ID NO: 32]
5'-TTATGGGGATTCGCCATCGCCAGTGGGATCTGGAAGGTGTGCA
GTTCCATCCAGAAAGTA-3'

[SEQ ID NO: 33]
5'-CGGAGCATAAATCGGCAGGATCACTTCATCGAAAGTCGCGCGT
GTAATTGCTGTTTGT-3'

The final PCR product was electroporated into the XQ37 strain (W3110 ΔlacI ΔspeE ΔspeG ΔargI ΔpuuP ΔpuuA PargECBH::Ptrc PspeF-potE::Ptrc) prepared in Example 2-2 to obtain an XQ39 strain (W3110 ΔlacI ΔspeE ΔspeG ΔargI ΔpuuP ΔpuuA PargECBH::Ptrc PspeF-potE::Ptrc PargD::Ptrc). The resultant cells were cultured in an agar medium containing chloroamphenicol, and only cells in which double homologous recombination occurred were selected. The presence of the trc promoter in the strain was confirmed by DNA sequence analysis.

2-4: Preparation of XQ43 Strain

Replacement of the native promoter of the speC gene with the trc promoter was performed as follows.

First PCR was performed using plasmid pECmulox as a template, the above-described primer of SEQ ID NO: 19 and a primer of SEQ ID NO: 36 below.

[SEQ ID NO: 36]
5'-TTTGCCCGATGCACGCCATCTCCTTACATTCTCTCGCTTATCG
CCGTTTCGACACTATAGAACGCGGCCG-3

Second PCR was performed using the first PCR product as a template and primers of SEQ ID NOS: 37 and 38 below.

[SEQ ID NO: 37]
5'-TGCCATGATTGCGCGAATTTTCTCCTCTCTGTACGGAGTTTGC
CCGATGCACGCCAT-3'

[SEQ ID NO: 38]
5'-TACTGGCGGCAATATTCATTGATTTCATGGTCTGTTTCCTGTG
TGAAATTGTTATCCGCTCACAATTCCACACAT-3'

Third PCR was performed using the second PCR product and primers of SEQ ID NOS: 39 and 40 below.

```
[SEQ ID NO: 39]
5'-GATGGCTTGTTTGTTCGCAAAGTCCTGGCTTGCACGCTTTAGC
GAAAGGTGCCATGATTGCGCGAATTT-3'

[SEQ ID NO: 40]
5'-ATCTCCCAACGCCACCACGCGACGATGAGAAGAAAGTCGGGAT
ACCAGTTCACTACTGGCGGCAATATTCATTGA-3'
```

The final PCR product was electroporated into the XQ39 strain (W3110 ΔlacI ΔspeE ΔspeG ΔargI ΔpuuP ΔpuuA PargECBH::Ptrc PspeF-potE::Ptrc PargD::Ptrc) prepared in (2-3) to obtain an XQ43 strain (W3110 ΔlacI ΔspeE ΔspeG ΔargI ΔpuuP ΔpuuA PargECBH::Ptrc PspeF-potE::Ptrc PargD::Ptrc PspeC::Ptrc). The resultant cells were cultured on an agar medium containing chloroamphenicol, and only cells in which double homologous recombination occurred were selected. The presence of the trc promoter was confirmed by DNA sequence analysis.

EXAMPLE 3

Production of Putrescine Using Mutant Microorganisms

Each of the mutant strains (*E. coli* K12 WL3110 mutants) of Table 1, prepared in Examples 1 and 2, was cultured in a flask containing a minimal R medium (containing 4 g/L $(NH_4)_2HPO_4$, 13.5 g/L $KH_2PO_4$, 1.7 g/L citric acid, 0.7 g/L $MgSO_4 \cdot 7H_2O$ and 0.5% (v/v) trace metal solution (Lee, S.Y. & Chang, H.N., *Biotechnol. Lett.*, 15: 971-974, 1993)). The trace metal solution contained (per liter): 5 M HCl, 10 g $FeSO_4 \cdot 7H_2O$, 2.25 g $ZnSO_4 \cdot 7H_2O$, 1 g $CuSO_4 \cdot 5H_2O$, 0.5 g $MnSO_4 \cdot 5H_2O$, 0.23 g $Na_2B_4O_7 \cdot 10H_2O$, 2 g $CaCl_2 \cdot 2H_2O$, and 0.1 g $(NH_4)_6Mo_7O_{24}$. A solution containing glucose (100 g/l) was sterilized separately and added to the sterilized medium to a final concentration of 10 g/l.

100 μl of each cell culture activated in an LB medium was inoculated into a preparative minimal medium and then cultured at 30° C. at 220 rpm for 24 hours until the maximum $OD_{600}$ reached 5. Then, 1 ml of the culture broth was added to a 350-mL baffled flask containing 50 ml of the same medium, and then was cultured at 30° C. at 220 rpm for 15 hours. The culture broth was centrifuged to separate cells, and the supernatant was analyzed by HPLC. Amines contained in the supernatant were detected by ophthaldialdehyde (OPA) derivation in a Hewlett Packard 1100 Series system (230 nm) using a C18-reverse phase column (buffer A: 45% 0.1 M sodium acetate, pH 7.2; buffer B: methanol. The analysis was carried out in the following conditions: 1-6 min 100% buffer A equilibration, 6-10 min linear gradient from 0 to 30% buffer B, 10-15 min gradient from 30% to 50% buffer B, 15-19 min gradient from 50% to 100% buffer B, 19-23 min gradient to 100% buffer B, and 23-25 min gradient from 100% to 30% buffer B, 25-28 min from 30% B to 100% A with a flow rate of 0.8 ml/min). Herein, a standard was used for calibration, and the concentrations of putrescine are presented in Table 1 below.

TABLE 1

| Strain | Genotype | Putrescine concentration (mg/L) |
|---|---|---|
| WL3110 | W3110 ΔlacI | 0 |
| XQ08 | W3110 ΔlacI ΔspeE | 0.65 |
| XQ17 | W3110 ΔlacI ΔpuuA | 0 |
| XQ22 | W3110 ΔlacI ΔpuuP ΔpuuA | 0.6 |
| XQ23 | W3110 ΔlacI ΔspeE ΔspeG ΔargI | 1.8 |
| XQ26 | W3110 ΔlacI ΔspeE ΔspeG ΔargI ΔpuuP ΔpuuA | 8.5 |
| XQ27 | W3110 ΔlacI ΔspeE ΔspeG ΔygjG ΔpuuP ΔpuuA | 4.2 |
| XQ29 | W3110 ΔlacI ΔspeE ΔspeG ΔygjG ΔargI ΔpuuP ΔpuuA | 8.5 |
| XQ33 | W3110 ΔlacI ΔspeE ΔspeG ΔargI ΔpuuP ΔpuuA PargECBH::Ptrc | 28.3 |
| XQ37 | W3110 ΔlacI ΔspeE ΔspeG ΔargI ΔpuuP ΔpuuA PargECBH::Ptrc PspeF-potE::Ptrc | 510 |
| XQ39 | W3110 ΔlacI ΔspeE ΔspeG ΔargI ΔpuuP ΔpuuA PargECBH::Ptrc PspeF-potE::Ptrc PargD::Ptrc | 820 |
| XQ43 | W3110 ΔlacI ΔspeE ΔspeG ΔargI ΔpuuP ΔpuuA PargECBH::Ptrc PspeF-potE::Ptrc PargD::Ptrc PspeC::Ptrc | 827 |

As can be seen in Table 1, in the mutant microorganisms in which the gene(s) (puuP, puuA, speE, speG, and argI) involved in the putrescine degradation or utilization pathway was deleted, putrescine productivity was increased depending on the kind and number of the deleted genes. The putrescine productivity was further increased when the promoter(s) of the argECBH gene encoding the operone for arginine biosynthesis, the argD gene encoding acetylornithine aminotransferase, the speF-potE gene encoding inducible ornithine decarboxylase and putrescine/ornithine antiporter and/or the speC gene encoding ornithine decarboxylase was replaced with the strong promoter.

EXAMPLE 4

Amplification of speC Gene Encoding Ornithine Decarboxylase

4-1: Preparation of Plasmid pKKSpeC

The speC gene encoding constitutive biosynthetic ornithine decarboxylase in *E. coli* W3110 was cloned into an expression vector pKK223-3 (Pharmacia Biotech, Uppsala, Sweden) inducing strong expression of the tac promoter. For this, PCR was performed using the genomic DNA of *E. coli* W3110 (derived from *E. coli* K-12, λ⁻, F⁻, prototrophic) as a template and primers of SEQ ID NOS: 34 and 35 below to obtain a speC fragment (2156 bp).

```
[SEQ ID NO: 34]:
5'-CAGCGAATTCATGAAATCAATGAATATTGCC-3'

[SEQ ID NO: 35]:
5'-CATTCTGCAGTTACTTCAACACATAACCGTA-3'
```

Next, the speC fragment (2,156 bp) and the pKK223-3 plasmid were treated with restriction enzymes (EcoRI and PstI) and then with T4 DNA ligase to fuse the speC fragment to the pKK223-3 plasmid to thereby produce a high copy number of a recombinant plasmid vector pKKSpeC.

4-2: Preparation of Plasmid p15SpeC

The speC gene encoding constitutive biosynthetic ornithine decarboxylase in *E. coli* W3110 was cloned into an expression vector pTac15K (p15A origin, low copies, KmR; KAISTMBEL stock) inducing strong expression of the tac promoter. For this, PCR was performed using the genomic DNA of *E. coli* W3110 (derived from *E. coli* K-12, λ−, F−, prototrophic) as a template and the above-described primers of SEQ ID NOS: 34 and 35 to obtain a speC fragment (2,156 bp).

Next, the speC fragment (2,156 bp) and the pTac15K plasmid were treated with restriction enzymes (EcoRI and PstI) and then with T4 DNA ligase to fuse the speC fragment to the pTac15K plasmid to thereby produce a low copy number of a recombinant plasmid vector p15SpeC.

4-3: Preparation of WL3110/pKKSpeC Strain

The pKKSpeC vector prepared in Example 4-1 was introduced into the WL3110 strain prepared in Example 1-1 to prepare a WL3110/pKKSpeC strain. The resultant cells were cultured on an agar medium containing ampicillin to thereby select transformed cell strains.

4-4: Preparation of XQ17/pKKSpeC Strain

The pKKSpeC vector prepared in Example 4-1 was introduced into the XQ17 strain prepared in Example 1-3 to prepare an XQ17/pKKSpeC strain. The resultant cells were cultured on an agar medium containing ampicillin to thereby select transformed cell strains.

4-5: Preparation of XQ22/pKKSpeC Strain

The pKKSpeC vector prepared in Example 4-1 was introduced into the XQ22 strain prepared in Example 1-4 to prepare an XQ22/pKKSpeC strain. The resultant cells were cultured on an agar medium containing ampicillin to thereby select transformed cell strains.

4-6: Preparation of XQ26/pKKSpeC Strain

The pKKSpeC vector prepared in Example 4-1 was introduced into the XQ26 strain prepared in Example 1-6 to prepare an XQ26/pKKSpeC strain. The resultant cells were cultured on an agar medium containing ampicillin to thereby select transformed cell strains.

4-7: Preparation of XQ33/pKKSpeC Strain

The pKKSpeC vector prepared in Example 4-1 was introduced into the XQ33 strain prepared in Example 2-1 to prepare an XQ33/pKKSpeC strain. The resultant cells were cultured on an agar medium containing ampicillin to thereby select transformed cell strains.

4-8: Preparation of XQ37/pKKSpeC Strain

The pKKSpeC vector prepared in Example 4-1 was introduced into the XQ37 strain prepared in Example 2-2 to prepare an XQ37/pKKSpeC strain. The resultant cells were cultured on an agar medium containing ampicillin to thereby select transformed cell strains.

4-9: Preparation of XQ39/pKKSpeC Strain

The pKKSpeC vector prepared in Example 4-1 was introduced into the XQ39 strain prepared in Example 2-3 to prepare an XQ39/pKKSpeC strain. The resultant cells were cultured on an agar medium containing ampicillin to thereby select transformed cell strains.

4-10: Preparation of XQ43/p15SpeC Strain

The p15SpeC vector prepared in Example 4-2 was introduced into the XQ43 strain prepared in Example 2-4 to prepare an XQ43/p15SpeC strain. The resultant cells were cultured on an agar medium containing ampicillin to thereby select transformed cell strains.

EXAMPLE 5

Production of Putrescine Using Mutant Microorganisms in which speC Gene Encoding Ornithine Decarboxylase is Amplified Each of the mutant strains prepared in Example 4 were cultured in a shake flask containing the same medium as described in Example 3.

100 μl of each cell culture activated in an LB medium was inoculated into a preparative minimal medium, and then cultured at 30° C. at 220 rpm for 30 hours until the maximum $OD_{600}$ reached 5. Then, 1 ml of the culture broth was added to a 350-mL baffled flask containing 50 ml of the same medium and then cultured at 30° C. at 220 rpm for 27 hours. The culture was centrifuged to separate cells, and the supernatant was analyzed by HPLC in the same conditions as described in Example 3. The results are presented in Table 2.

TABLE 2

| Strain/plasmid | Putrescine concentration (mg/L) |
|---|---|
| WL3110/pKKSpeC | 220 |
| XQ17/pKKSpeC | 368 |
| XQ22/pKKSpeC | 400 |
| XQ26/pKKSpeC | 433 |
| XQ33/pKKSpeC | 910 |
| XQ37/pKKSpeC | 1100 |
| XQ39/pKKSpeC | 1189 |
| XQ43/p15SpeC | 1317 |

As can be seen in Table 2, the putrescine-producing abilities of the mutant microorganisms (WL3110/pKKSpeC, XQ17/pKKSpeC, XQ22/pKKSpeC, XQ26/pKKSpeC, XQ33/pKKSpeC, XQ37/pKKSpeC, XQ39/pKKSpeC and XQ43/p15SpeC) expressing ornithine decarboxylase and having reduced putrescine degradation and utilization activities were significantly increased compared to those of the mutant microorganisms (WL3110, XQ17, XQ22, XQ26, XQ33, XQ37, XQ39 and XQ43) of Table 1 in which neither pKKSpeC nor p15SpeC was introduced.

EXAMPLE 6

Production of Putrescine Through Fed-Batch Culture of XQ37/pKKSpeC Strain

Figure 2:
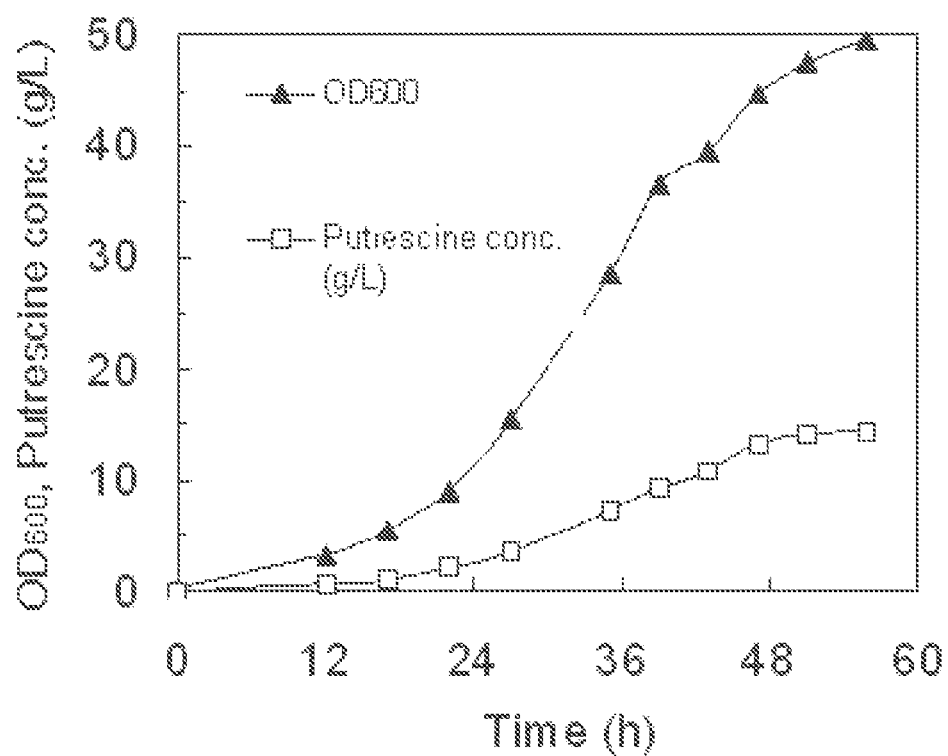
FIG. 2 is a graphic diagram showing the production of putrescine from XQ37/pKKSpeC cells through fed-batch fermentation using glucose.

The potential of reduced putrescine degradation and utilization activity, together with decarboxylase activity, was analyzed through fed-batch fermentation. The fed-batch fermentation was performed in a 6.6-liter fermentor (Bioflo 3000; New Brunswick Scientific Co., Edison, N.J.) after adding 10 g/l glucose to 2 liters of a minimal R medium. 1 ml of the XQ37/pKKSpeC culture activated in an LB medium was added to a 350-mL baffled flask containing 50 ml of the same medium, and then cultured at 30° C. at 220 rpm for 24 hours until the maximum $OD_{600}$ reached 5. 200 ml of the preculture was used for inoculation into the fermentor. Dissolved oxygen in the fermented broth was maintained with 20% saturated air by automatically increasing an agitation speed of 850 rpm. When the pH of the fermented broth was increased by about 0.2 pH units from a fixed pH of 6.8 as a result of glucose exhaustion, the glucose-containing solution was automatically added in order to increase the glucose concentration to more than 3 g/l. The glucose-containing solution contained 500 g/l glucose and 200 g/l $(NH_4)_2SO_4$. Throughout the entire fermentation period except a short time for which pH was increased due to glucose exhaustion, the pH of the fermented broth was maintained at pH 6.8 by adding 28% (v/v) ammonia solution. The fermented broth was sampled and centrifuged to separate cells, and the supernatant was analyzed by HPLC in the same manner as described in Example 3. The results are shown in FIG. 2. As shown in FIG. 2, the XQ37/pKKSpeC strain produced 14.3 g/l of putrescine after 55.8 hours of the inoculation, and the maximum putrescine productivity was 0.28 $gL^{-1} h^{-1}$ after 47 hours of the inoculation.

EXAMPLE 7

Production of Putrescine Through Fed-Batch Culture of XQ39 Strain

Figure 3:
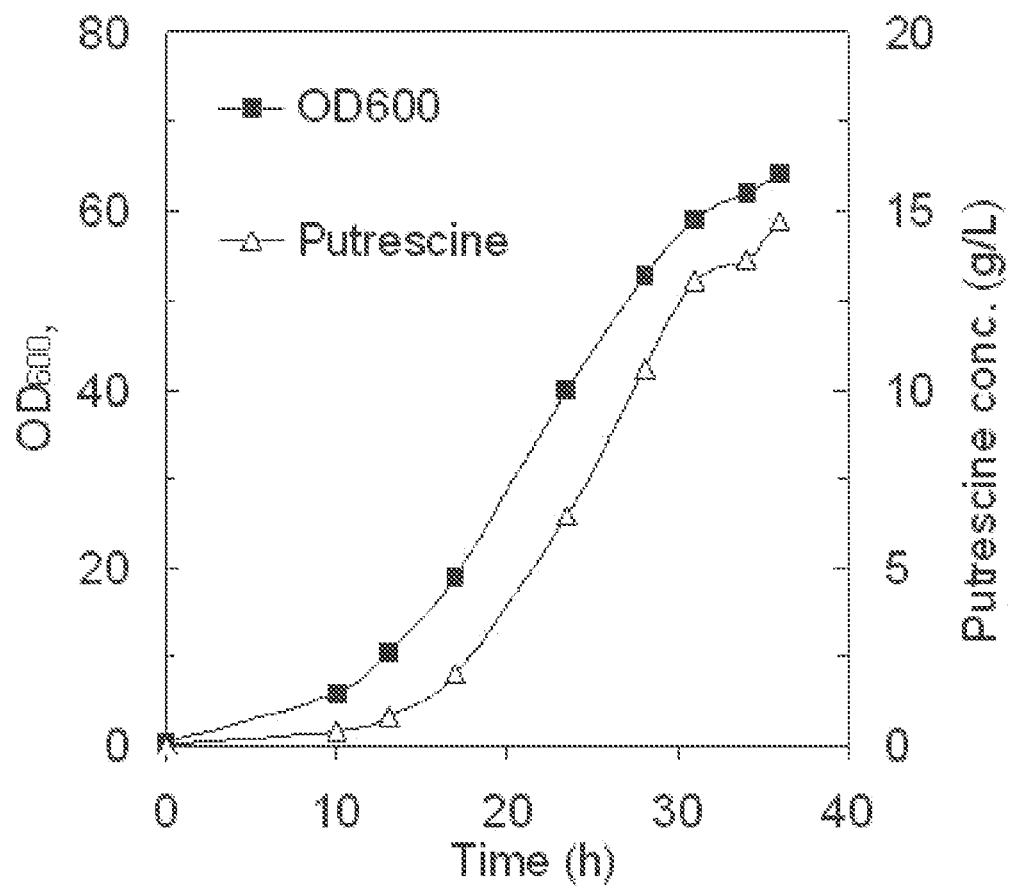
FIG. 3 is a graphic diagram showing the production of putrescine from XQ39 cells through fed-batch fermentation using glucose.

Fed-batch fermentation was carried out in the same manner as described in Example 6, except that the XQ39 strain was used instead of the XQ37/pKKSpeC strain. The fermented broth was analyzed by HPLC, and the results are shown in FIG. 3. As shown in FIG. 3, the XQ39 strain produced 14.7 g/l after 36 hours of the inoculation, and the maximum putrescine productivity was 0.42 g $L^{-1} h^{-1}$ after 31 hours of the inoculation.

EXAMPLE 8

Production of Putrescine Through Fed-Batch Culture of XQ43 Strain

The XQ43 strain prepared in Example 2 was cultured in a flask containing 50 ml of a minimal R/2 medium (containing 2 g/L $(NH_4)_2HPO_4$, 6.75 g/L $KH_2PO_4$, 0.85 g/L citric acid, 0.7 g/L $MgSO_4.7H_2O$, 0.5% (v/v) trace metal solution) (Qian et al., Biotechnol. and Bioeng, 101(3): 587-601, 2008) supplemented with 3 g/L of $(NH_4)_2SO_4$.

The trace metal solution contained (per liter): 5 M HCl, 10 g $FeSO_4.7H_2O$, 2.25 g $ZnSO_4.7H_2O$, 1 g $CuSO_4.5H_2O$, 0.5 g $MnSO_4.5H_2O$, 0.23 g $Na_2B_4O_7.10H_2O$, 2 g $CaCl_2.2H_2O$, and 0.1 g $(NH_4)_6Mo_7O_{24}$. A solution containing glucose (100 g/l) was sterilized separately and added to the sterilized medium to a final concentration of 10 g/l. 1 ml of the XQ43 culture activated in an LB medium was added to a 350-mL baffled flask containing 50 ml of the above-described medium, and then cultured at 37° C. at 220 rpm for 24 hours until the $OD_{600}$ of the culture reached 3.3. 200 ml of the preculture was used for inoculation into a fermentor. Dissolved oxygen in the culture was maintained with 20% saturated air by automatically increasing an agitation speed of 1000 rpm.

Figure 4:
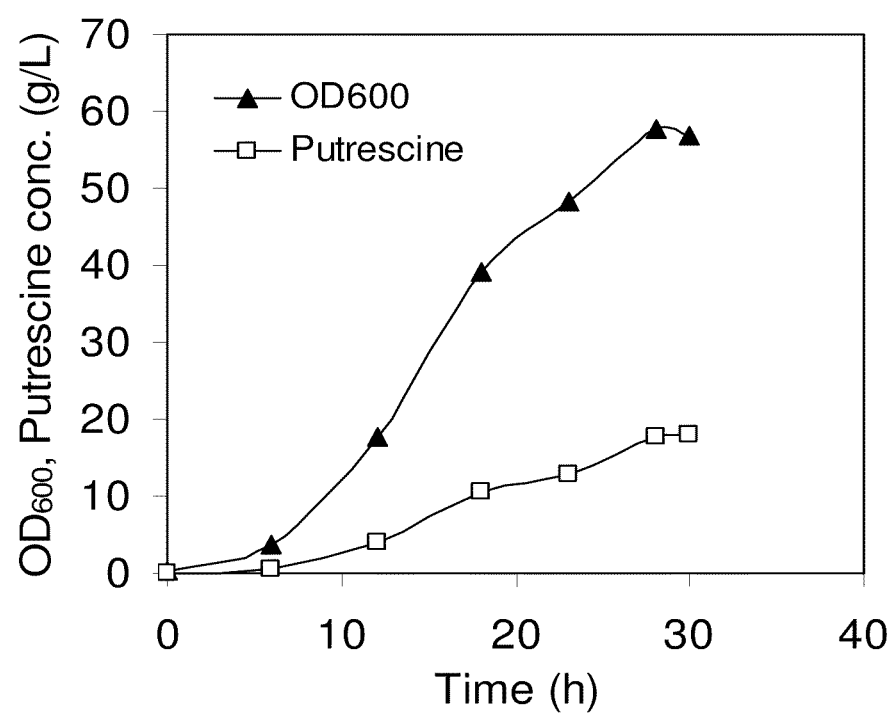
FIG. 4 is a graphic diagram showing the production of putrescine from XQ43 cells through fed-batch fermentation using glucose.

The fed-batch fermentation of the XQ43 strain was carried out in a 6.6-liter fermentor (Bioflo 3000; New Brunswick Scientific Co., Edison, N.J.) after adding 10 g/l of glucose. When the pH of the fermented broth was increased by about 0.01 pH units from a fixed pH of 6.8 as a result of glucose exhaustion, a glucose-containing solution was automatically added in order to increase the glucose concentration to more than 2 g/l. The glucose-containing solution contained 522 g/l of glucose, 8 g/L of $MgSO_4$ and 170 g/L of $(NH_4)_2SO_4$. Throughout the entire fermentation period except a short time for which pH was increased due to glucose exhaustion, the pH of the fermented broth was maintained at 6.8 by adding 10 M KOH solution. The fermented broth was sampled and centrifuged to separate cells, and the supernatant was analyzed by HPLC in the same manner as described in Example 3. The results are shown in FIG. 4. As shown in FIG. 4, the XQ43 strain produced 18.0 g/l of putrescine after 30 hours of the inoculation, and the maximum putrescine productivity was 0.63 g $L^{-1} h^{-1}$ after 28 hours of the inoculation.

EXAMPLE 9

Production of Putrescine Through Fed-Batch Culture of XQ43/p15SpeC Strain

Figure 5:
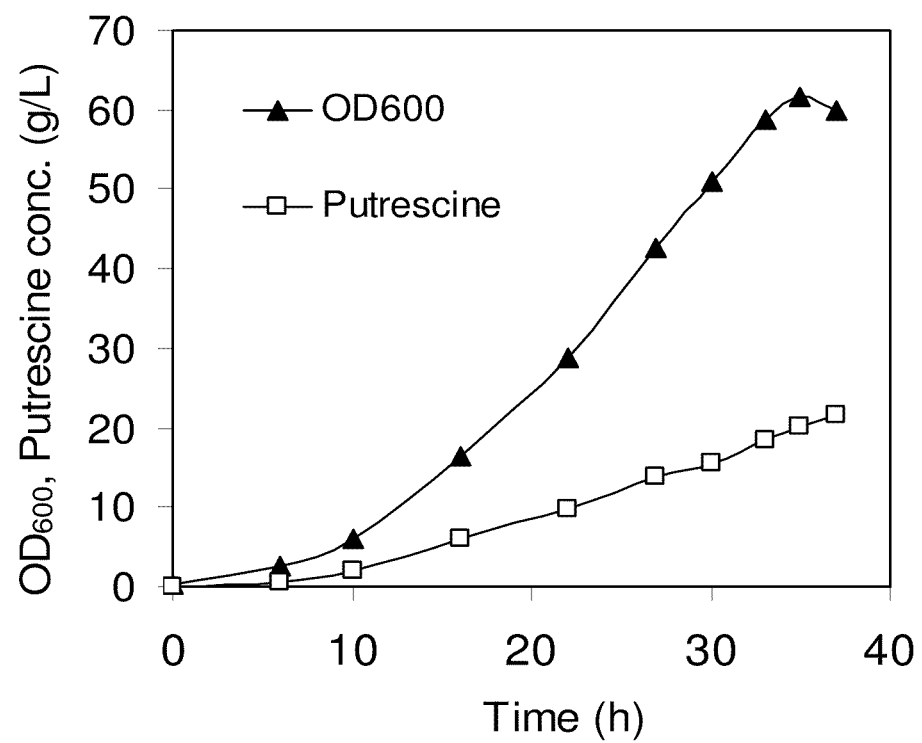
FIG. 5 is a graphic diagram showing the production of putrescine from XQ43/p15SpeC cells through fed-batch fermentation using glucose.

Fed-batch fermentation was carried out in the same manner as described in Example 8, except that the XQ43/p15SpeC strain was used instead of the XQ43 strain. The fermented broth was analyzed by HPLC, and the results are shown in FIG. 5. As shown in FIG. 5, the XQ43/p15SpeC strain produced 21.7 g/l of putrescine after 37 hours of the inoculation, and the maximum putrescine productivity was 0.58 g $L^{-1} h^{-1}$ after 37 hours of the inoculation.

As described in detail above, the present invention provides mutant microorganisms having the ability to produce putrescine. These mutant microorganisms are useful for producing a high concentration of putrescine which can be widely used in various industrial applications.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A mutant microorganism isolated having the ability to produce putrescine wherein at least one gene selected from the group consisting of a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway, is inactivated or deleted and wherein a promoter of at least one gene selected from the group consisting of an argECBH gene encoding an operon for arginine biosynthesis, an argD gene encoding acetylornithine aminotransferase, and a speFpotE gene encoding inducible ornithine decarboxylase and putrescine/ornithine antiporter is replaced with a strong promoter ; and wherein at least one gene selected from the group consisting of a puuA gene encoding γ-glutamylputrescine synthase, a ygjG gene encoding putrescine transaminase and an argF gene encoding ornithine carbamoyltransferase chain F-monomer is further inactivated or deleted; and a speC gene encoding ornithine decarboxylase is further introduced or amplified.

2. The mutant microorganism of claim 1, wherein a lacl gene encoding a lac operon repressor is further deleted to increase the expression of genes encoding enzymes involved in putrescine biosynthesis.

3. The mutant microorganism of claim 1, wherein the speC gene encoding ornithine decarboxylase is introduced in the form of an expression vector containing a strong promoter.

4. The mutant microorganism of claim 1, wherein the strong promoter is selected from the group consisting of a trc promoter, a tac promoter, a T7 promoter, a lac promoter and a trp promoter.

5. The mutant microorganism of claim 1, wherein the microorganism is selected from the group consisting of *Bacillus* sp., *Corynebacterium* sp., *Escherichia* sp., *Pichia* sp., *Pseudomonas* sp., and *Saccharomyces* sp.

6. A method of preparing a mutant microorganism having the ability to produce putrescine, the method comprising: inactivating or deleting at least one gene selected from the group consisting of a speE gene encoding spermidine synthase, a speG gene encoding spermidine N-acetyltransferase, an argI gene encoding ornithine carbamoyltransferase chain I-monomer and a puuP gene encoding putrescine importer, which are involved in the putrescine degradation or utilization pathway, from a microorganism having a putrescine production pathway; and introducing or amplifying a speC gene encoding ornithine decarboxylase, before or after the inactivation or deletion.

7. The method of claim 6, wherein at least one gene elected from the group consisting of a puuA gene encoding y-glutamylputrescine synthase, a ygjG gene encoding putrescine transaminase and an argF gene encoding ornithine carbamoyltransferase chain F-monomer is further inactivated or deleted.

8. The method of claim 6, wherein a lacl gene encoding a lac operon repressor is further deleted to increase the expression of genes encoding enzymes involved in putrescine biosynthesis.

9. The method of claim 6, wherein the spec gene encoding ornithine decarboxylase is introduced in the form of an expression vector containing a strong promoter.

10. The method of claim 9, wherein the strong promoter is selected from the group consisting of a trc promoter, a tac promoter, a T7 promoter, a lac promoter and a trp promoter.

11. The method of claim 9, wherein the expression vector is pKKSpeC or pl5SpeC.

12. The method of claim 6, wherein the microorganism is selected from the group consisting of *Bacillus* sp., *Corynebacterium* sp., *Escherichia* sp., *Pichia* sp., *Pseudomonas* sp., and *Saccharomyces* sp.

13. A method for preparing a mutant microorganism having the ability to produce putrescine, the method comprising:
    a) inactivating or deleting at least one gene selected from the group consisting of a speE gene encoding spermidine synthase, a speG gene encoding spermidine Nacetyltransferase, an argI gene encoding ornithine carbamoyltransferase chain Imonomer and a puuP gene encoding putrescine importer, which are involved in the putrescine degradation or utilization pathway, from a microorganism having a putrescine production pathway; and
    b) replacing a promoter of at least one gene selected from the group consisting of an argECBH gene encoding an operon for arginine biosynthesis, an argD gene encoding acetylornithine aminotransferase, and a speF-potE gene encoding inducible ornithine decarboxylase and putrescinelornithine antiporter with a trc promoter.

14. The method of claim 13, wherein in step a), at least one gene elected from the group consisting of a puuA gene encoding y-glutamylputrescine synthase, a ygjG gene encoding putrescine transaminase and an argF gene encoding ornithine carbamoyltransferase chain F-monomer is further inactivated or deleted.

15. The method of claim 13, wherein in step a), a lacl gene encoding a lac operon repressor is further deleted to increase the expression of genes encoding enzymes involved in putrescine biosynthesis.

16. The method of claim 13, further comprising introducing or amplifying a spec gene encoding ornithine decarboxylase, before step a), after step b) and between steps a) and b).

17. The method of claim 16, wherein the spec gene encoding ornithine decarboxylase is introduced in the form of an expression vector containing a strong promoter.

18. The method of claim 13, wherein the strong promoter is selected from the group consisting of a trc promoter, a tac promoter, a T7 promoter, a lac promoter and a trp promoter.

19. The method of claim 17, wherein the expression vector is pKKSpeC or pl5SpeC.

20. The method of claim 13, wherein the microorganism is selected from the group consisting of *Bacillus* sp., *Corynebacterium* sp., *Escherichia* sp., *Pichia* sp., *Pseudomonas* sp., and *Saccharomyces* sp.

21. A method for producing putrescine, the method comprising:
    culturing the mutant microorganism of claim 1 to produce putrescine; and recovering putrescine from the culture broth.

22. A method for producing putrescine, the method comprising:
    culturing the mutant microorganism of claim 1 to produce putrescine; and recovering putrescine from the culture broth.

23. The mutant microorganism of claim 3, wherein the strong promoter is selected from the group consisting of a trc promoter, a tac promoter, a T7 promoter, a lac promoter and a trp promoter.

24. The method of claim 17, wherein the strong promoter is selected from the group consisting of a trc promoter, a tac promoter, a T7 promoter, a lac promoter and a trp promoter.

* * * * *

SEQUENCE LISTING

<160> NUMBER OF SEQ ID NOS: 40

<210> SEQ ID NO 1
<211> LENGTH: 73
<212> TYPE: DNA
<213> ORGANISM: Artificial
<220> FEATURE:
<223> OTHER INFORMATION: primer 1

<400> SEQUENCE: 1

```
gtgaaaccag taacgttata cgatrtcgca gagtatgccg gtgtctctta gattggcagc      60
attacacgtc ttg                                                         73
```

<210> SEQ ID NO 2
<211> LENGTH: 70
<212> TYPE: DNA
<213> ORGANISM: Artificial
<220> FEATURE:
<223> OTHER INFORMATION: primer 2

<400> SEQUENCE: 2

```
tcactgcccg ctttccagtc gggaaacctg tcgtgccagc tgcattaatg cacttaacgg      60
ctgacatggg                                                             70
```

<210> SEQ ID NO 3
<211> LENGTH: 70
<212> TYPE: DNA
<213> ORGANISM: Artificial
<220> FEATURE:
<223> OTHER INFORMATION: primer 3

<400> SEQUENCE: 3

```
cgcctgaata atttcggttg agagatggcg taaggcgtcg ttatctgtcg gacactatag      60
aacgcggccg                                                             70
```

<210> SEQ ID NO 4
<211> LENGTH: 70
<212> TYPE: DNA
<213> ORGANISM: Artificial
<220> FEATURE:
<223> OTHER INFORMATION: primer 4

<400> SEQUENCE: 4

```
atgttgcgcc ctttttttac gggtgttaac aaaggaggta tcaacccatg ccgcataggc      60
cactagtgga                                                             70
```

<210> SEQ ID NO 5
<211> LENGTH: 70
<212> TYPE: DNA
<213> ORGANISM: Artificial
<220> FEATURE:
<223> OTHER INFORMATION: primer 5

<400> SEQUENCE: 5

```
gatgaaacaa ccccgcaagg ggtattacgc gttttttcaac atccactcaa gacactatag     60
aacgcggccg                                                             70
```

<210> SEQ ID NO 6
<211> LENGTH: 70
<212> TYPE: DNA
<213> ORGANISM: Artificial
<220> FEATURE:

<223> OTHER INFORMATION: primer 6

<400> SEQUENCE: 6
cgagcggaaa acaaaccaaa ggcgaagaat catggaaacc aatatcgttg ccgcataggc    60
cactagtgga    70

<210> SEQ ID NO 7
<211> LENGTH: 70
<212> TYPE: DNA
<213> ORGANISM: Artificial
<220> FEATURE:
<223> OTHER INFORMATION: primer 7

<400> SEQUENCE: 7
tcaccatcat acaacggcac tttgcgatag cggcggatca gataccataa gacactatag    60
aacgcggccg    70

<210> SEQ ID NO 8
<211> LENGTH: 70
<212> TYPE: DNA
<213> ORGANISM: Artificial
<220> FEATURE:
<223> OTHER INFORMATION: primer 8

<400> SEQUENCE: 8
cgcctgaata atttcggttg agagatggcg taaggcgtcg ttatctgtcg gacactatag    60
aacgcggccg    70

<210> SEQ ID NO 9
<211> LENGTH: 70
<212> TYPE: DNA
<213> ORGANISM: Artificial
<220> FEATURE:
<223> OTHER INFORMATION: primer 9

<400> SEQUENCE: 9
atgttgcgcc cttttttttac gggtgttaac aaaggaggta tcaacccatg ccgcataggc    60
cactagtgga    70

<210> SEQ ID NO 10
<211> LENGTH: 69
<212> TYPE: DNA
<213> ORGANISM: Artificial
<220> FEATURE:
<223> OTHER INFORMATION: primer 10

<400> SEQUENCE: 10
aatgtaagga cacgttatgc caagcgccca cagtgttaag ctacgcccgg acactataga    60
acgcggccg    69

<210> SEQ ID NO 11
<211> LENGTH: 70
<212> TYPE: DNA
<213> ORGANISM: Artificial
<220> FEATURE:
<223> OTHER INFORMATION: primer 11

<400> SEQUENCE: 11
ctattgtgcg gtcggcttca ggagagtctg acccggtgtt ttgtgctctg ccgcataggc    60
cactagtgga    70

<210> SEQ ID NO 12

-continued

```
<211> LENGTH: 70
<212> TYPE: DNA
<213> ORGANISM: Artificial
<220> FEATURE:
<223> OTHER INFORMATION: primer 12

<400> SEQUENCE: 12
taatgtgatg ccgggatggt ttgtatttcc cggcatcttt atagcgatag gacactatag    60
aacgcggccg                                                            70

<210> SEQ ID NO 13
<211> LENGTH: 70
<212> TYPE: DNA
<213> ORGANISM: Artificial
<220> FEATURE:
<223> OTHER INFORMATION: primer 13

<400> SEQUENCE: 13
ccatataaat tgaattttaa ttcattgagg cgttagccac aggagggatc ccgcataggc    60
cactagtgga                                                            70

<210> SEQ ID NO 14
<211> LENGTH: 71
<212> TYPE: DNA
<213> ORGANISM: Artificial
<220> FEATURE:
<223> OTHER INFORMATION: primer 14

<400> SEQUENCE: 14
atagcaatag aacactttgg gtggaagaat agacctatca ctgcataaaa taatgtgatg    60
ccgggatggt t                                                          71

<210> SEQ ID NO 15
<211> LENGTH: 70
<212> TYPE: DNA
<213> ORGANISM: Artificial
<220> FEATURE:
<223> OTHER INFORMATION: primer 15

<400> SEQUENCE: 15
ccacctttgt gacaaagatt tatgctttag acttgcaaat gaataatcat ccatataaat    60
tgaattttaa                                                            70

<210> SEQ ID NO 16
<211> LENGTH: 70
<212> TYPE: DNA
<213> ORGANISM: Artificial
<220> FEATURE:
<223> OTHER INFORMATION: primer 16

<400> SEQUENCE: 16
ctgcaatact taaatcggta tcatgtgata cgcgagcctc cggagcatat gacactatag    60
aacgcggccg                                                            70

<210> SEQ ID NO 17
<211> LENGTH: 70
<212> TYPE: DNA
<213> ORGANISM: Artificial
<220> FEATURE:
<223> OTHER INFORMATION: primer 17

<400> SEQUENCE: 17
cgtcgtatcg ccatccgatt tgatattacg cttcttcgac acttactcgc ccgcataggc    60
```
cactagtgga                                                                  70

<210> SEQ ID NO 18
<211> LENGTH: 75
<212> TYPE: DNA
<213> ORGANISM: Artificial
<220> FEATURE:
<223> OTHER INFORMATION: primer 18

<400> SEQUENCE: 18
tatccgctca caattccaca cattatacga gccggatgat taattgtcaa cagctgacac    60
tatagaacgc ggccg                                                     75

<210> SEQ ID NO 19
<211> LENGTH: 75
<212> TYPE: DNA
<213> ORGANISM: Artificial
<220> FEATURE:
<223> OTHER INFORMATION: primer 19

<400> SEQUENCE: 19
tatccgctca caattccaca cattatacga gccggatgat taattgtcaa cagctccgca    60
taggccacta gtgga                                                     75

<210> SEQ ID NO 20
<211> LENGTH: 75
<212> TYPE: DNA
<213> ORGANISM: Artificial
<220> FEATURE:
<223> OTHER INFORMATION: primer 20

<400> SEQUENCE: 20
cgctggcacc cacaatcagc gtattcaaca tggtctgttt cctgtgtgaa attgttatcc    60
gctcacaatt ccaca                                                     75

<210> SEQ ID NO 21
<211> LENGTH: 75
<212> TYPE: DNA
<213> ORGANISM: Artificial
<220> FEATURE:
<223> OTHER INFORMATION: primer 21

<400> SEQUENCE: 21
tctcgataaa tggcggtaat ttgtttttca tggtctgttt cctgtgtgaa attgttatcc    60
gctcacaatt ccaca                                                     75

<210> SEQ ID NO 22
<211> LENGTH: 75
<212> TYPE: DNA
<213> ORGANISM: Artificial
<220> FEATURE:
<223> OTHER INFORMATION: primer 22

<400> SEQUENCE: 22
atgttcatat gcggatggcg atttacatag gtcactagct ctgcgccagc gtagccgctg    60
gcacccacaa tcagc                                                     75

<210> SEQ ID NO 23
<211> LENGTH: 75
<212> TYPE: DNA
<213> ORGANISM: Artificial
<220> FEATURE:
<223> OTHER INFORMATION: primer 23

-continued

<400> SEQUENCE: 23
tcgagtgcct cttccgtggc gcttattgaa ggtgtggcaa tcagagcgcg gtaaatctcg    60
ataaatggcg gtaat                                                    75

<210> SEQ ID NO 24
<211> LENGTH: 62
<212> TYPE: DNA
<213> ORGANISM: Artificial
<220> FEATURE:
<223> OTHER INFORMATION: primer 24

<400> SEQUENCE: 24
actaagggca cttcagcgta caggtcttcc tgactctctg tagacactat agaacgcggc    60
cg                                                                  62

<210> SEQ ID NO 25
<211> LENGTH: 60
<212> TYPE: DNA
<213> ORGANISM: Artificial
<220> FEATURE:
<223> OTHER INFORMATION: primer 25

<400> SEQUENCE: 25
agcttcgact ttcacttctt caatgcccgt tagtctaccg actaagggca cttcagcgta    60

<210> SEQ ID NO 26
<211> LENGTH: 75
<212> TYPE: DNA
<213> ORGANISM: Artificial
<220> FEATURE:
<223> OTHER INFORMATION: primer 26

<400> SEQUENCE: 26
aatcactaac cgcaattttt aattttgaca tggtctgttt cctgtgtgaa attgttatcc    60
gctcacaatt ccaca                                                    75

<210> SEQ ID NO 27
<211> LENGTH: 60
<212> TYPE: DNA
<213> ORGANISM: Artificial
<220> FEATURE:
<223> OTHER INFORMATION: primer 27

<400> SEQUENCE: 27
aaggcggaca actcatatta tgaagtttgc tcatcgcaat agcttcgact ttcacttctt    60

<210> SEQ ID NO 28
<211> LENGTH: 77
<212> TYPE: DNA
<213> ORGANISM: Artificial
<220> FEATURE:
<223> OTHER INFORMATION: primer 28

<400> SEQUENCE: 28
cgactttcat taatgtagat acattctcgc tgcgtggtaa aacagtccgg gcaagaatca    60
ctaaccgcaa tttttaa                                                  77

<210> SEQ ID NO 29
<211> LENGTH: 60
<212> TYPE: DNA
<213> ORGANISM: Artificial
<220> FEATURE:
<223> OTHER INFORMATION: primer 29

```
<400> SEQUENCE: 29
caactgctgg ctaatttcct gcatcgctga tttctgattg gacactatag aacgcggccg      60

<210> SEQ ID NO 30
<211> LENGTH: 60
<212> TYPE: DNA
<213> ORGANISM: Artificial
<220> FEATURE:
<223> OTHER INFORMATION: primer 30

<400> SEQUENCE: 30
gcagttccat ccagaaagta ttcttagcga acaaggacat caactgctgg ctaatttcct      60

<210> SEQ ID NO 31
<211> LENGTH: 75
<212> TYPE: DNA
<213> ORGANISM: Artificial
<220> FEATURE:
<223> OTHER INFORMATION: primer 31

<400> SEQUENCE: 31
cgcgtgtaat tgctgtttgt tcaattgcca tggtctgttt cctgtgtgaa attgttatcc      60
gctcacaatt ccaca                                                      75

<210> SEQ ID NO 32
<211> LENGTH: 60
<212> TYPE: DNA
<213> ORGANISM: Artificial
<220> FEATURE:
<223> OTHER INFORMATION: primer 32

<400> SEQUENCE: 32 ttatgggat tcgccatcgc cagtgggatc tggaaggtgt gcagttccat ccagaaagta       60

<210> SEQ ID NO 33
<211> LENGTH: 58
<212> TYPE: DNA
<213> ORGANISM: Artificial
<220> FEATURE:
<223> OTHER INFORMATION: primer 33

<400> SEQUENCE: 33
cggagcataa atcggcagga tcacttcatc gaaagtcgcg cgtgtaattg ctgtttgt        58

<210> SEQ ID NO 34
<211> LENGTH: 31
<212> TYPE: DNA
<213> ORGANISM: Artificial
<220> FEATURE:
<223> OTHER INFORMATION: primer 34

<400> SEQUENCE: 34
cagcgaattc atgaaatcaa tgaatattgc c                                    31

<210> SEQ ID NO 35
<211> LENGTH: 31
<212> TYPE: DNA
<213> ORGANISM: Artificial
<220> FEATURE:
<223> OTHER INFORMATION: primer 35

<400> SEQUENCE: 35
cattctgcag ttacttcaac acataaccgt a                                    31

<210> SEQ ID NO 36
```

```
<211> LENGTH: 70
<212> TYPE: DNA
<213> ORGANISM: Artificial
<220> FEATURE:
<223> OTHER INFORMATION: primer 36

<400> SEQUENCE: 36
tttgcccgat gcacgccatc tccttacatt ctctcgctta tcgccgtttc gacactatag    60
aacgcggccg                                                            70

<210> SEQ ID NO 37
<211> LENGTH: 57
<212> TYPE: DNA
<213> ORGANISM: Artificial
<220> FEATURE:
<223> OTHER INFORMATION: primer 37

<400> SEQUENCE: 37
tgccatgatt gcgcgaattt tctcctctct gtacggagtt tgcccgatgc acgccat       57

<210> SEQ ID NO 38
<211> LENGTH: 75
<212> TYPE: DNA
<213> ORGANISM: Artificial
<220> FEATURE:
<223> OTHER INFORMATION: primer 38

<400> SEQUENCE: 38
tactggcggc aatattcatt gatttcatgg tctgtttcct gtgtgaaatt gttatccgct    60
cacaattcca cacat                                                      75

<210> SEQ ID NO 39
<211> LENGTH: 69
<212> TYPE: DNA
<213> ORGANISM: Artificial
<220> FEATURE:
<223> OTHER INFORMATION: primer 39

<400> SEQUENCE: 39
gatggcttgt ttgttcgcaa agtcctggct tgcacgcttt agcgaaaggt gccatgattg    60
cgcgaattt                                                             69

<210> SEQ ID NO 40
<211> LENGTH: 75
<212> TYPE: DNA
<213> ORGANISM: Artificial
<220> FEATURE:
<223> OTHER INFORMATION: primer 40

<400> SEQUENCE: 40
atctcccaac gccaccacgc gacgatgaga agaaagtcgg gataccagtt cactactggc    60
ggcaatattc attga                                                      75
```